US009145591B1

(12) United States Patent
Exner

(10) Patent No.: US 9,145,591 B1
(45) Date of Patent: Sep. 29, 2015

(54) **DETECTION OF *MYCOBACTERIUM TUBERCULOSIS* COMPLEX NUCLEIC ACIDS**

(75) Inventor: Maurice Exner, Mission Viejo, CA (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 123 days.

(21) Appl. No.: 13/587,599

(22) Filed: Aug. 16, 2012

Related U.S. Application Data

(62) Division of application No. 11/075,825, filed on Mar. 8, 2005, now Pat. No. 8,263,330.

(51) Int. Cl.
C07H 21/04 (2006.01)
C12Q 1/68 (2006.01)

(52) U.S. Cl.
CPC ...................................... *C12Q 1/689* (2013.01)

(58) Field of Classification Search
None
See application file for complete search history.

(56) References Cited

U.S. PATENT DOCUMENTS

| | | | |
|---|---|---|---|
| 5,538,848 A | 7/1996 | Livak et al. | |
| 5,691,146 A | 11/1997 | Mayrand | |
| 5,723,591 A | 3/1998 | Livak et al. | |
| 5,736,333 A | 4/1998 | Livak et al. | |
| 5,866,336 A | 2/1999 | Nazarenko et al. | |
| 5,876,930 A | 3/1999 | Livak et al. | |
| 5,952,202 A | 9/1999 | Aoyagi et al. | |
| 6,030,787 A | 2/2000 | Livak et al. | |
| 6,258,569 B1 | 7/2001 | Livak et al. | |
| 6,582,908 B2 * | 6/2003 | Fodor et al. | 506/9 |
| 6,815,165 B2 | 11/2004 | Lee et al. | |
| 2003/0073657 A1* | 4/2003 | Halle et al. | 514/44 |

OTHER PUBLICATIONS

NEB catalog (1998/1999 pp. 121, 284).*
Buck, et al., "Rapid, Simple Method for Treating Clinical Specimens Containing *Mycobacterium tuberculosis* to Remove DNA for Polymerase Chain Reaction" *J. Clin. Microbiol.* 30:1331-1334 (1992).
Desjardin et al., "Comparison of the ABI 7700 (TaqMan) and Competitive PCR for Quantification of IS6110 DNA in Sputum During Treatment of Tuberculosis" *J. Clin. Microbiol.* 36(7):1964-1968 (1998).
Fang and Forbes, "A *Mycobacterium tuberculosis* IS6110 Preferential Locus (ipl) for Insertion into the Genome" *J Clin Microbiol.* 35:479-481 (1997).
Fang et al., "IS6110-Mediated Deletions of Wild-Type Chromosomes of *Mycobacterium tuberculosis*" *J Bacteriol* 181:1014-1020 (1999).
Fang et al., "Characterization of 1S1547, a New Member of the IS900 Family in the *Mycobacterium tuberculosis* Complex, and Its Association with IS6110" *J Bacteriol* 181:1021-1024 (1999).
Hafner et al., "Isothermal Amplification and Multimerization of DNA by *Bst* DNA Polymerase" *BioTechniques* 30:852-867 (2001).
Goh et al., "Rapid Differentiation of "*Mycobacterium canettii*" from Other *Mycobacterium tuberculosis* Complex Organisms by PCR-Restriction Analysis of he *hsp65* Gene" *J Clin Microbiol.* 39:3705-3708 (2001).
Murray and Nardell, "Molecular Epidemiology of Tuberculosis: Achievements and Challenges to Current Knowledge" *Bulletin of the World Health Organization* 80(6):477-482 (2002).
Saiki, R., "Amplification of Genomic DNA" *PCR Protocols: A Guide to Methods and Applications*. Edited by Michael A. Innis et al., Chapter 2, pp. 13-20 (1990).
Tyagi et al., "Multicolor Molecular Beacons for Allele Discrimination" *Nature Biotechnology* 16:49-53 (1998).
Wharam et al., "Specific Detection of DNA and RNA Targets Using a Novel Isothermal Nucleic Acid Amplification Assay Based on the Formation of a Three-Way Junction Structure" *Nucleic Acids Res.* 29:1-8 (2001).
Dean et al., Comprehensive human genome amplification using multiple displacement amplification. PNAS, 99(8): 5261-5266, 2002.
Dean et al., Rapid amplification of plasmid and phage DNA using Phi29 DNA polymerase and multiply-primed rolling circle amplification. Genome Res., 11: 1095-1099, 2001.
Sambrook et al., *Molecular Cloning, A Laboratory Manual*, Chapter 14, "In Vitro amplification of DNA by the polymerase chain reaction," p. 14.1-14.35, 1989.
Wang et al., DNA amplification method tolerant to sample degradation. Genome Res., 14:2357-2366, 2004.
Park, "Detection and Identification of Mycobacteria by Amplification of the Internal Transcribed Spacer Regions with Genus-and Species-Specific PCR Primers," Journal of Clinical Microbiology, vol. 38, No. 11, pp. 4080-4085, Nov. 2000.
Hermans et al., "Specific Dectection of *Mycobacterium tuberculosis* Complex Strains by Polymerase Chain Reaction," Journal of Clinical Microbiology, vol. 28, No. 6, pp. 1204-1213, Jun. 1990.
GenBank Accession No. X98158 NCBI, "*Mybacterium tuberculosis*," Jul. 7, 2002.
Desjardin et al., "Comparison of the ABI 7700 System (TaqMan) and Competitive PCR for Quantification of IS6110 DNA in Sputum during Treatment of Tuberculosis," Journal of Clinical Microbiology, vol. 36, No. 7, Jul. 1998.
Office Action issued by the Examiner in U.S. Appl. No. 11/075,825 on Jun. 27, 2007.
Office Action issued by the Examiner in U.S. Appl. No. 11/075,825 on Oct. 18, 2007.
Office Action issued by the Examiner in U.S. Appl. No. 11/075,825 on May 14, 2008.
Office Action issued by the Examiner in U.S. Appl. No. 11/075,825 on Nov. 28, 2008.
Office Action issued by the Examiner in U.S. Appl. No. 11/075,825 on Oct. 13, 2009.
Office Action issued by the Examiner in U.S. Appl. No. 11/075,825 on Oct. 28, 2010.
Office Action issued by the Examiner in U.S. Appl. No. 11/075,825 on Apr. 14, 2011.
Office Action issued by the Examiner in U.S. Appl. No. 11/075,825 on Sep. 29, 2011.
Notice of Allowance issued by the Examiner in U.S. Appl. No. 11/075,825 on May 4, 2012.

* cited by examiner

*Primary Examiner* — Katherine Salmon
(74) *Attorney, Agent, or Firm* — Foley & Lardner LLP

(57) ABSTRACT

Disclosed is a method for determining the presence of *Mycobacterium tuberculosis* complex nucleic acids in a test sample. In particular, regions of the IS6110 preferential locus (ipl) 3'-flanking region of the *Mycobacterium tuberculosis* complex genome are amplified and detected. In addition, oligonucleotides that can be used as primers to amplify the ipl 3'-flanking region and probe oligonucleotides are described.

10 Claims, 5 Drawing Sheets

```
  1  gacctttatg tctcagtgtc ggtgttgtgt gtgccgcgag gtgggtgtgt cggtgtgaca
 61  gacgccgtgt cgcggtggtt tgttccggat cacctggtgt ctggctcact ttgcgtctgc
121  cgtcctcttg gggttggcgt tgagcagtat tgccggcact aggtgagaag gaccggccgg
181  cgtgacttga taggagcgtg gctttcgccc cgactgagat gtgtccgccg accggcccaa
241  cctcaacacc ccctcaagtg aaggaggcaa ccaccatggt tgttgttgga accgatgcgc
301  acaagtacag ccacaccttt gtggccaccg acgaagtggg tcgccaactc ggtgagaaga
361  ccgtcaaggc caccacggcc gggcacgcca cagccatcat gtgggcccgt gaacagttcg
421  gcctcgagct gatctggggc atcgaggact gccgcaacat gtcggcgcgt ctggagcgtg
481  acctactggc ggccggccag caggtggtgc gggtacccac caagctgatg gcccagaccc
541  gcaagtcggc gcgcagtcgg ggcaagtcgg atccgatcga tgcactgacg gtggcgcggg
601  cggtgctgcg tgaaaccgac ctaccoctgg ccacccacga cgagacgtcg
```

Fig. 1

```
ipl_X95799    ------------------------------------------------GACCTTTATGT
ipl2_X98151   GCTGCCTACTACGCTCAACGCCAGAGACCAGCCGCCGGCTGAGGTCTCAGATCAGAGAGT
ipl6_X98158   ------------------------------------------GCTGCCTACTACG-
ipl1_X98149   ------------------------------------------------------------
ipl5_X98156   ------------------------------------------------------------
ipl3_X98153   ------------------------------------------------------------ ipl_X95799    CTCAG----TGTCGGTGTTGTGTGTGCCGCGAGGTGGGTGTGTCGGTGTGACAGACGCCG
ipl2_X98151   CTCCGGACTCACCGGGGCGGT-TCAGCCGCGAGGTGGGTGTGTCGGTGTGACAGACGCCG
ipl6_X98158   CTCAA----CGCCAGAG----ACCAGCCGCCGGCTGAGGTCTCAGATCAGAGAGTCTCCG
ipl1_X98149   ------------------------------------------------------------
ipl5_X98156   ------------------------------------------------------------
ipl3_X98153   ------------------------------------------------------------ ipl_X95799    TG-TCGCGGTGGTTTGTTCCGGATCACCTGGTGTCTGGCTCACTTTGCGTCTGCCGTCCT
ipl2_X98151   TG-TCGCGGTGGTTTGTTCCGGATCACCTGGTGTCTGGCTCACTTTGCGTCTGCCGTCCT
ipl6_X98158   GACTCACCGGGG-------CGGTTCA---GGTGTCTGGCTCACTTTGCGTCTGCCGTCCT
ipl1_X98149   ------------------------------------------------------------
ipl5_X98156   ------------------------------------------------------------
ipl3_X98153   ------------------------------------------------------------ ipl_X95799    CTTGGGGTTGGCGTTGAGCAGTATTGCCGGCACTAGGTGAGAAGGACCGGCCGGCGTGAC
ipl2_X98151   CTTGGGGTTGGCGTTGAGCAGTATTGCCGGCACTAGGTGAGAAGGACCGGCCGGCGTGAC
ipl6_X98158   CTTGGGGTTGGCGTTGAGCAGTATTGCCGGCACTAGGTGAGAAGGACCGGCCGGCGTGAC
ipl1_X98149   -----------GCTGCCTACTACGCTCAACGCCAGAGACCAGCCGCCGGCTGAGGTC-T
ipl5_X98156   -----------GCTGCCTACTACGCTCAACGCCAGAGACCAGCCGCCGGCTGAGGTC-T
ipl3_X98153   -----------GCTGCCTACTACGCTCAACGCCAGAGACCAGCCGCCGGCTGAGGTC-T
                         * **   * **     *   * **      *      * *****  *  ** ipl_X95799    TTGATAGGAGCGTGGCTTTCGCCCCGACTGAGATGTGTCCGCCGACCGGC----------
ipl2_X98151   TTGATAGGAGCGTGGCTTTCGCCCCGACTGAGATGTGTCCGCCGACCGGC----------
ipl6_X98158   TTGATAGGAGCGTGGCTTTCGCCCCGACTGAGATGTGTCCGCCGACCGGC----------
ipl1_X98149   CAGATCAGAGAGT---CTCCGGACTCACCGGGGCG-GTTCA------------------
ipl5_X98156   CAGATCAGAGAGT---CTCCGGACTCACCGGGGCG-GTTCAC-----------------
ipl3_X98153   CAGATCAGAGAGT---CTCCGGACTCACCGGGGCG-GTTCAGAGCGTGGCTTTCGCCCCG
                * * **      *     * *   * **  * ipl_X95799    -----------------------CCAACCTCAACACCCCCTCAAGTGAAGGAGG
ipl2_X98151   -----------------------CCAACCTCAACACCCCCTCAAGTGAAGGAGG
ipl6_X98158   -----------------------CCAACCTCAACACCCCCTCAAGTGAAGGAGG
ipl1_X98149   -----------------------------------------------GAGG
ipl5_X98156   -----------------------CCAACCTCAACACCCCCTCAAGTGAAGGAGG
ipl3_X98153   ACTGAGATGTGTCCGCCGACCGGCCCAACCTCAACACCCCCTCAAGTGAAGGAGG
                                                                    ********
```

Fig. 1 (Con't.)

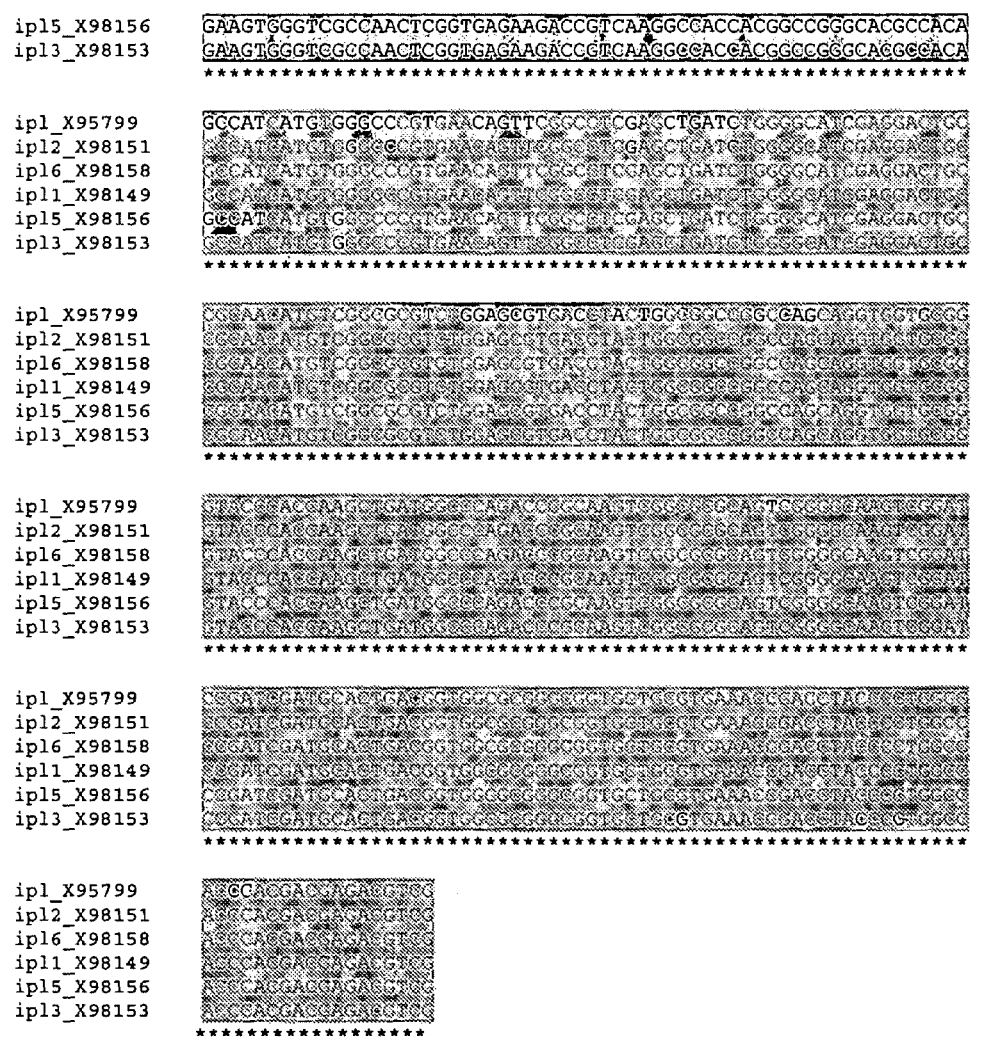

ipl5_X98156  GAAGTGGGTCGCCAACTCGGTGAGAAGACCGTCAAGGCCACCACGGCCGGGCACGCCACA
ipl3_X98153  GAAGTGGGTCGCCAACTCGGTGAGAAGACCGTCAAGGCCACGACGGCCGGGCACGCCACA
             ************************************************************

Fig. 1 (Con't.)

```
ipl_X95799   --------------------------------------------------GACCTTTATGT
ipl2_X98151  GCTGCCTACTACGCTCAACGCCAGAGACCAGCCGCCGGCTGAGGTCTCAGATCAGAGAGT
ipl6_X98158  --------------------------------------------------GCTGCCTACTACG-
ipl1_X98149  ------------------------------------------------------------
ipl5_X98156  ------------------------------------------------------------
ipl3_X98153  ------------------------------------------------------------ ipl_X95799   CTCAG----TGTCGGTGTTGTGTGTGCCGCGAGGTGGGTGTGTCGGTGTGACAGACGCCG
ipl2_X98151  CTCCGGACTCACCGGGGCGGT-TCAGCCGCGAGGTGGGTGTGTCGGTGTGACAGACGCCG
ipl6_X98158  CTCAA----CGCCAGAG----ACCAGCCGCCGGCTGAGGTCTCAGATCAGAGAGTCTCCG
ipl1_X98149  ------------------------------------------------------------
ipl5_X98156  ------------------------------------------------------------
ipl3_X98153  ------------------------------------------------------------ ipl_X95799   TG-TCGCGGTGGTTTGTTCCGGATCACCTGGTGTCTGGCTCACTTTGCGTCTGCCGTCCT
ipl2_X98151  TG-TCGCGGTGGTTTGTTCCGGATCACCTGGTGTCTGGCTCACTTTGCGTCTGCCGTCCT
ipl6_X98158  GACTCACCGGGG--------CGGTTCA---GGTGTCTGGCTCACTTTGCGTCTGCCGTCCT
ipl1_X98149  ------------------------------------------------------------
ipl5_X98156  ------------------------------------------------------------
ipl3_X98153  ------------------------------------------------------------ ipl_X95799   CTTGGGGTTGGCGTTGAGCAGTATTGCCGGCACTAGGTGAGAAGGACCGGCCGGCGTGAC
ipl2_X98151  CTTGGGGTTGGCGTTGAGCAGTATTGCCGGCACTAGGTGAGAAGGACCGGCCGGCGTGAC
ipl6_X98158  CTTGGGGTTGGCGTTGAGCAGTATTGCCGGCACTAGGTGAGAAGGACCGGCCGGCGTGAC
ipl1_X98149  ------------GCTGCCTACTACGCTCAACGCCAGAGACCAGCCGCCGGCTGAGGTC-T
ipl5_X98156  ------------GCTGCCTACTACGCTCAACGCCAGAGACCAGCCGCCGGCTGAGGTC-T
ipl3_X98153  ------------GCTGCCTACTACGCTCAACGCCAGAGACCAGCCGCCGGCTGAGGTC-T
                         *  **    *   * **      *    * **   *    ***** *   ** ipl_X95799   TTGATAGGAGCGTGGCTTTCGCCCCGACTGAGATGTGTCCGCCGACCGGC-----------
ipl2_X98151  TTGATAGGAGCGTGGCTTTCGCCCCGACTGAGATGTGTCCGCCGACCGGC-----------
ipl6_X98158  TTGATAGGAGCGTGGCTTTCGCCCCGACTGAGATGTGTCCGCCGACCGGC-----------
ipl1_X98149  CAGATCAGAGAGT---CTCCGGACTCACCGGGGCG-GTTCA--------------------
ipl5_X98156  CAGATCAGAGAGT---CTCCGGACTCACCGGGGCG-GTTCAC-------------------
ipl3_X98153  CAGATCAGAGAGT---CTCCGGACTCACCGGGGCG-GTTCAGAGCGTGGCTTTCGCCCCG
               *   * **       * **     *  ** *    *  **  * ipl_X95799   -----------------------------CCAACCTCAACACCCCCTCAAGTGAAGGAGGCAACC
ipl2_X98151  -----------------------------CCAACCTCAACACCCCCTCAAGTGAAGGAGGCAACC
ipl6_X98158  -----------------------------CCAACCTCAACACCCCCTCAAGTGAAGGAGGCAACC
ipl1_X98149  --------------------------------------------------GAGGCAACC
ipl5_X98156  -----------------------------CCAACCTCAACACCCCCTCAAGTGAAGGAGGCAACC
ipl3_X98153  ACTGAGATGTGTCCGCCGACCGGCCCAACCTCAACACCCCCTCAAGTGAAGGAGGCAACC
                                                              ******** ipl_X95799   ACCATGGTTGTTGTTGGAACCGATGCGCACAAGTACAGCCACACCTTTGTGGCCACCGAC
ipl2_X98151  ACCATGGTTGTTGTTGGAACCGATGCGCACAAGTACAGCCACACCTTTGTGGCCACCGAC
ipl6_X98158  ACCATGGTTGTTGTTGGAACCGATGCGCACAAGTACAGCCACACCTTTGTGGCCACCGAC
ipl1_X98149  ACCATGGTTGTTGTTGGAACCGATGCGCACAAGTACAGCCACACCTTTGTGGCCACCGAC
ipl5_X98156  ACCATGGTTGTTGTTGGAACCGATGCGCACAAGTACAGCCACACCTTTGTGGCCACCGAC
ipl3_X98153  ACCATGGTTGTTGTTGGAACCGATGCGCACAAGTACAGCCACACCTTTGTGGCCACCGAC
             ************************************************************ ipl_X95799   GAAGTGGGTCGCCAACTCGGTGAGAAGACCGTCAAGGCCACCACGGCCGGGCACGCCACA
ipl2_X98151  GAAGTGGGTCGCCAACTCGGTGAGAAGACCGTCAAGGCCACCACGGCCGGGCACGCCACA
ipl6_X98158  GAAGTGGGTCGCCAACTCGGTGAGAAGACCGTCAAGGCCACCACGGCCGGGCACGCCACA
ipl1_X98149  GAAGTGGGTCGCCAACTCGGTGAGAAGACCGTCAAGGCCACCACGGCCGGGCACGCCACA
```

Fig. 2

```
ip15_X98156    GAAGTGGGTCGCCAACTCGGTGAGAAGACCGTCAAGGCCACCACGGCCGGGCACGCCACA
ip13_X98153    GAAGTGGGTCGCCAACTCGGTGAGAAGACCGTCAAGGCCACCACGGCCGGGCACGCCACA
               ************************************************************ ip1_X95799     GCCATCATCTCGGCCCGTGAACAGTTCCGCCTCGAGCTGATCTCGGGCCATCGAGGACTGC
ip12_X98151    GCCATCATGTCGGCCCGTGAACAGTTCCGGCCTCGAGCTGATCTGGGGCATCGAGGACTGC
ip16_X98158    GCCATCATGTCGGCCCGTGAACAGTTCGGCCTCGAGCTGATCTGGGGCATCGAGGACTGC
ip11_X98149    GCCATCATCTCGGCCCGTGAACAGTTCGCCCTCGAGCTGATCTGGGGCATCGAGGACTGC
ip15_X98156    GCCATCATGTCGGCCCGTGAACAGTTCCGCCTCGAGCTGATCTGGGGCATCGAGGACTGC
ip13_X98153    GCCATCATGTCGGCCCGTGAACAGTTCGGCCTCGAGCTGATCTGGGGCATCGAGGACTGC
               ************************************************************ ip1_X95799     CGCAACATGTCGGCGCGTCTGGAGCGTGACCTACTGGCGGCCCGGCCAGCAGGTGGTGCGG
ip12_X98151    CGCAACATGTCGGCGCGTCTGGAGCGTGACCTACTGGCGGCCCGGCCAGCAGGTGGTGCGG
ip16_X98158    CGCAACATGTCGGCGCGTCTGGAGCGTGACCTACTGGCGGCCGGCCAGCAGGTGGTGCGG
ip11_X98149    CGCAACATGTCGGCGCGTCTGGAGCGTGACCTACTGGCGGCCCGGCCAGCAGGTGGTGCGG
ip15_X98156    CGCAACATGTCGGCGCGTCTGGAGCGTGACCTACTGGCGGCCCGGCCAGCAGGTGGTGCGG
ip13_X98153    CGCAACATGTCGGCGCGTCTGGAGCGTGACCTACTGGCGGCCGGCCAGCAGGTGGTGCGG
               ************************************************************ ip1_X95799     GTACCCACCAAGCTGATGGCCCAGACCCGCAAGTCGGCGCGCAGTCGGGGCAAGTCGGAT
ip12_X98151    GTACCCACCAAGCTGATGGCCCAGACCCGCAAGTCGGCGCGCAGTCGGGGCAAGTCGGAT
ip16_X98158    GTACCCACCAAGCTGATGGCCCAGACCCGCAAGTCGGCGCGCAGTCGGGGCAAGTCGGAT
ip11_X98149    GTACCCACCAAGCTGATGGCCCAGACCCGCAAGTCGGCGCGCAGTCGGGGCAAGTCGGAT
ip15_X98156    GTACCCACCAAGCTGATGGCCCAGACCCGCAAGTCGGCGCGCAGTCGGGGCAAGTCGGAT
ip13_X98153    GTACCCACCAAGCTGATGGCCCAGACCCGCAAGTCGGCGCGCAGTCGGGGCAAGTCGGAT
               ************************************************************ ip1_X95799     CCGATCGATGCACTGACGGTGGCGCGGGCGGTGCTGCGTGAAACCGACCTACCCCTGGCC
ip12_X98151    CCGATCGATGCACTGACGGTGGCGCGGGCGGTGCTGCGTGAAACCGACCTACCCCTGGCC
ip16_X98158    CCGATCGATGCACTGACGGTGGCGCGGGCGGTGCTGCGTGAAACCGACCTACCCCTGGCC
ip11_X98149    CCGATCGATGCACTGACGGTGGCGCGGGCGGTGCTGCGTGAAACCGACCTACCCCTGGCC
ip15_X98156    CCGATCGATGCACTGACGGTGGCGCGGGCGGTGCTGCGTGAAACCGACCTACCCCTGGCC
ip13_X98153    CCGATCGATGCACTGACGGTGGCGCGGGCGGTGCTGCGTGAAACCGACCTACCCCTGGCC
               ************************************************************ ip1_X95799     ACCCACGACGAGACGTCG
ip12_X98151    ACCCACGACGAGACGTCG
ip16_X98158    ACCCACGACGAGACGTCG
ip11_X98149    ACCCACGACGAGACGTCG
ip15_X98156    ACCCACGACGAGACGTCG
ip13_X98153    ACCCACGACGAGACGTCG
               ******************
```

Fig. 2 (Con't.)

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctcggtgaga agaccgtca                                                  19

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtcctcgatg ccccagat                                                   18

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
agctcgaggc cgaactgttc ac                                              22

<210> SEQ ID NO 4
<211> LENGTH: 650
<212> TYPE: DNA
<213> ORGANISM: Mycobacterium tuberculosis

<400> SEQUENCE: 4
gacctttatg tctcagtgtc ggtgttgtgt gtgccgcgag gtgggtgtgt cggtgtgaca      60
gacgccgtgt cgcggtggtt tgttccggat cacctggtgt ctggctcact ttgcgtctgc     120
cgtcctcttg ggggttggcgt tgagcagtat tgccggcact aggtgagaag gaccggccgg    180
cgtgacttga taggagcgtg gctttcgccc cgactgagat gtgtccgccg accggcccaa    240
cctcaacacc ccctcaagtg aaggaggcaa ccaccatggt tgttgttgga accgatgcgc    300
```

```
acaagtacag ccacacctttt gtggccaccg acgaagtggg tcgccaactc ggtgagaaga    360
ccgtcaaggc caccacggcc gggcacgcca cagccatcat gtgggcccgt gaacagttcg    420
gcctcgagct gatctggggc atcgaggact gccgcaacat gtcggcgcgt ctggagcgtg    480
acctactggc ggccggccag caggtggtgc gggtacccac caagctgatg cccagaccc     540 gcaagtcggc gcgcagtcgg ggcaagtcgg atccgatcga tgcactgacg gtggcgcggg    600
cggtgctgcg tgaaaccgac ctaccccctgg ccacccacga cgagacgtcg              650

<210> SEQ ID NO 5
<211> LENGTH: 383
<212> TYPE: DNA
<213> ORGANISM: Mycobacterium tuberculosis

<400> SEQUENCE: 5
caaccaccat ggttgttgtt ggaaccgatg cgcacaagta cagccacacc tttgtggcca     60
ccgacgaagt gggtcgccaa ctcggtgaga agaccgtcaa ggccaccacg gccgggcacg    120
ccacagccat catgtgggcc cgtgaacagt tcggcctcga gctgatctgg ggcatcgagg    180
actgccgcaa catgtcggcg cgtctggagc gtgacctact ggcggccggc cagcaggtgg    240
tgcgggtacc caccaagctg atggcccaga cccgcaagtc ggcgcgcagt cggggcaagt    300
cggatccgat cgatgcactg acggtggcgc gggcggtgct gcgtgaaacc gacctacccc    360
tggccaccca cgacgagacg tcg                                            383

<210> SEQ ID NO 6
<211> LENGTH: 702
<212> TYPE: DNA
<213> ORGANISM: Mycobacterium tuberculosis

<400> SEQUENCE: 6
gctgcctact acgctcaacg ccagagacca gccgccggct gaggtctcag atcagagagt     60
ctccggactc accggggcgg ttcagccgcg aggtgggtgt gtcggtgtga cagacgccgt    120
gtcgcggtgg tttgttccgg atcacctggt gtctggctca cttttgcgtct gccgtcctct    180 tggggttggc gttgagcagt attgccggca ctaggtgaga aggaccggcc ggcgtgactt    240
gataggagcg tggctttcgc cccgactgag atgtgtccgc cgaccggccc aacctcaaca    300
ccccctcaag tgaaggaggc aaccaccatg gttgttgttg gaaccgatgc gcacaagtac    360
agccacacct tgtggccac cgacgaagtg ggtcgccaac tcggtgagaa gaccgtcaag    420
gccaccacgc ccgggcacgc cacagccatc atgtgggccc gtgaacagtt cggcctcgag    480
ctgatctggg gcatcgagga ctgccgcaac atgtcggcgc gtctggagcg tgacctactg    540
gcggccggcc agcaggtggt gcgggtaccc accaagctga tggcccagac ccgcaagtcg    600
gcgcgcagtc ggggcaagtc ggatccgatc gatgcactga cggtggcgcg gcggtgctg    660 cgtgaaaccg acctacccct ggccacccac gacgagacgt cg                       702

<210> SEQ ID NO 7
<211> LENGTH: 639
<212> TYPE: DNA
<213> ORGANISM: Mycobacterium tuberculosis

<400> SEQUENCE: 7
gctgcctact acgctcaacg ccagagacca gccgccggct gaggtctcag atcagagagt     60
ctccggactc accggggcgg ttcaggtgtc tggctcactt tgcgtctgcc gtcctcttgg    120
```

```
ggttggcgtt gagcagtatt gccggcacta ggtgagaagg accggccggc gtgacttgat      180
aggagcgtgg ctttcgcccc gactgagatg tgtccgccga ccggcccaac ctcaacaccc      240
cctcaagtga aggaggcaac caccatggtt gttgttggaa ccgatgcgca caagtacagc      300
cacacctttg tggccaccga cgaagtgggt cgccaactcg gtgagaagac cgtcaaggcc      360
accacggccg ggcacgccac agccatcatg tgggcccgtg aacagttcgg cctcgagctg      420
atctggggca tcgaggactg ccgcaacatg tcggcgcgtc tggagcgtga cctactggcg      480
gccggccagc aggtggtgcg ggtacccacc aagctgatgg cccagacccg caagtcggcg      540
cgcagtcggg gcaagtcgga tccgatcgat gcactgacgg tggcgcgggc ggtgctgcgt      600
gaaaccgacc taccctggc cacccacgac gagacgtcg                              639

<210> SEQ ID NO 8
<211> LENGTH: 471
<212> TYPE: DNA
<213> ORGANISM: Mycobacterium tuberculosis

<400> SEQUENCE: 8
gctgcctact acgctcaacg ccagagacca gccgccggct gaggtctcag atcagagagt       60
ctccggactc accggggcgg ttcagaggca accaccatgg ttgttgttgg aaccgatgcg      120
cacaagtaca gccacacctt gtggccacc gacgaagtgg gtcgccaact cggtgagaag      180
accgtcaagg ccaccacggc cgggcacgcc acagccatca tgtgggcccg tgaacagttc      240
ggcctcgagc tgatctgggg catcgaggac tgccgcaaca tgtcggcgcg tctggagcgt      300
gacctactgg cggccggcca gcaggtggtg cgggtaccca ccaagctgat ggcccagacc      360
cgcaagtcgg cgcgcagtcg gggcaagtcg gatccgatcg atgcactgac ggtggcgcgg      420
gcggtgctgc gtgaaaccga cctacccctg gccacccacg acgagacgtc g              471

<210> SEQ ID NO 9
<211> LENGTH: 499
<212> TYPE: DNA
<213> ORGANISM: Mycobacterium tuberculosis

<400> SEQUENCE: 9
gctgcctact acgctcaacg ccagagacca gccgccggct gaggtctcag atcagagagt       60
ctccggactc accggggcgg ttcacccaac ctcaacaccc cctcaagtga aggaggcaac      120
caccatggtt gttgttggaa ccgatgcgca caagtacagc cacacctttg tggccaccga      180
cgaagtgggt cgccaactcg gtgagaagac cgtcaaggcc accacggccg ggcacgccac      240
agccatcatg tgggcccgtg aacagttcgg cctcgagctg atctggggca tcgaggactg      300
ccgcaacatg tcggcgcgtc tggagcgtga cctactggcg gccggccagc aggtggtgcg      360
ggtacccacc aagctgatgg cccagacccg caagtcggcg cgcagtcggg gcaagtcgga      420
tccgatcgat gcactgacgg tggcgcgggc ggtgctgcgt gaaaccgacc taccctggc      480 cacccacgac gagacgtcg                                                  499

<210> SEQ ID NO 10
<211> LENGTH: 541
<212> TYPE: DNA
<213> ORGANISM: Mycobacterium tuberculosis

<400> SEQUENCE: 10
gctgcctact acgctcaacg ccagagacca gccgccggct gaggtctcag atcagagagt       60
ctccggactc accggggcgg ttcagagcgt ggctttcgcc ccgactgaga tgtgtccgcc      120
```

```
gaccggccca acctcaacac cccctcaagt gaaggaggca accaccatgg ttgttgttgg    180
aaccgatgcg cacaagtaca gccacacctt tgtggccacc gacgaagtgg gtcgccaact    240
cggtgagaag accgtcaagg ccaccacggc cgggcacgcc acagccatca tgtgggcccg    300
tgaacagttc ggcctcgagc tgatctgggg catcgaggac tgccgcaaca tgtcggcgcg    360
tctggagcgt gacctactgg cggccggcca gcaggtggtg cgggtaccca ccaagctgat    420
ggcccagacc cgcaagtcgg cgcgcagtcg gggcaagtcg gatccgatcg atgcactgac    480
ggtggcgcgg gcggtgctgc gtgaaaccga cctacccctg gccacccacg acgagacgtc    540
g                                                                   541
```

DETECTION OF *MYCOBACTERIUM TUBERCULOSIS* COMPLEX NUCLEIC ACIDS

FIELD OF THE INVENTION

The present invention relates to methods and nucleotide sequences for amplifying and detecting of *Mycobacterium tuberculosis* complex in a biological sample.

BACKGROUND OF THE INVENTION

Tuberculosis (TB) is a chronic disease caused by *Mycobacterium tuberculosis* (*M. tuberculosis*). Tuberculosis is contagious and is spread by airborne bacilli from the lungs of an infectious person. Approximately one-third of the world's population are carriers of *M. tuberculosis*, most of whom are asymptomatic. Approximately 5-10% of those infected with *M. tuberculosis* will become sick or infectious at some point in their lifetime. In the United States, nearly 15,000 new cases of tuberculosis were reported in 2003. The incidence is much higher in South East Asia and parts of Africa.

Persons infected with both the HIV virus and *M. tuberculosis* are particularly susceptible to developing tuberculosis. The weakened immune system of an HIV-infected increases the likelihood the individual will become sick with tuberculosis. Presently, it is estimated that about 15 million patients are infected by both the *M. tuberculosis* and HIV and having tuberculosis accounts for approximately 13% of deaths in AIDS patients.

The genus *Mycobacterium* contains approximately 50 species. The best known and widest spread diseases caused by mycobacteria are leprosy, caused by *M. leprae*, and tuberculosis caused by *M. tuberculosis*. Most other mycobacteria normally occur only as environmental saprophytes. However, saprophytic mycobacterial species also cause opportunist diseases, which happens often, but not exclusively, in individuals suffering from suppressed immune systems, such as AIDS patients or individuals undergoing immuno-suppression therapy. The opportunist strains comprise the slow-growing species *M. avium*, and the closely related *M. intracellulare* and *M. scrofulaceum* (often together referred to as the MAIS complex), *M. kansai*, *M. marinum* and *M. ulcerans*, and the fast-growing species *M. chelonae* and *M. fortultum*. Although quite rare in the Western world for several decades, the occurrence of opportunist mycobacterial diseases and tuberculosis has shown a significant increase with the incidence of AIDS. Further, it has been reported that mycobacteria are involved in the etiology of a plurality of other diseases, such as sarcoidosis and Crohn's disease, as well as different auto-immune diseases, such as auto-immune dermatitis, rheumatoid arthritis and diabetes. It has been suggested that this role can be attributed to a structural mimicry between epitopes of mycobacteria and those of the host organism.

A rapid clinical diagnosis of *M. tuberculosis* infection has important clinical and therapeutic implications because of the morbidity associated with the disease and the possibility for further spread of this disease. Although presumptive diagnosis of tuberculosis can be made on the basis of patient histories, clinical and radiological findings, and the presence of acid-fast bacilli in patient specimens, the isolation of *M. tuberculosis* is required for the definitive diagnosis of tuberculosis. Smear tests of sputum samples are considered the least sensitive technique for diagnosis of TB because the estimated number of bacteria required for a positive test is relatively high. Routine cultures are cumbersome and time-consuming.

Early efforts aimed at differentiating among strains of *M. tuberculosis* on a nucleic acid level largely failed until the discovery of polymorphic sites within repetitive sequences of the genome were identified. IS6110 is a transposable element that is currently the most widely used marker for differentiating strains of *M. tuberculosis* (Murray and Nardell, Bulletin of the World Health Organization 80(6):477-482, 2002). IS6110 is found in multiple copies throughout the genome of *M. tuberculosis* and is preferentially inserted into a sequence of DNA termed the IS6110 preferential locus, ipl. The ipl locus is a stretch of 267 nucleotides that contains 6 sites for IS6110 insertion. The ipl locus corresponds to the first 267 nucleotides of GenBank Accession No. X95799 (SEQ ID NO:4); no insertion sites have been found in the 3'-flanking region (nucleotides 268 through 650 of SEQ ID NO:4) of this sequence. (Fang and Forbes, J Clin Microbiol 35:479-81, 1997; Fang et al., J Bacteriol 181:1014-20, 1999; Fang et al., J Bacteriol 181:1021-4, 1999).

A *Mycobacterium tuberculosis* (MT) complex of organisms has been identified and includes organisms which are closely related species of the genus *Mycobacterium* and which cause a tuberculosis-like syndrome. MT complex organisms share a high degree of evolutionary conservation and include *M. tuberculosis*, *M. bovis*, *M. bovis* BCG, *M. Africanum*, *M. Microti*, and *M. canettii*.

Polymerase chain reaction ("PCR") has been widely utilized to improve the sensitivity of standard hybridization methods. U.S. Pat. No. 6,815,165 discloses a method and kit which uses PCR to specifically detect *M. tuberculosis* DNA in a test sample. Hybridization assays using self-quenching fluorescence probes with and/or without internal controls for detection of nucleic acid application products are known in the art, for example, U.S. Pat. Nos. 6,258,569; 6,030,787; 5,952,202; 5,876,930; 5,866,336; 5,736,333; 5,723,591; 5,691,146; and 5,538,848. In addition, the detection of *M. tuberculosis* using Real-time PCR (Taqman systems) has been described by Desjardin et al., J. Clin. Microbiol. 36(7): 1964-1968, 1998.

SUMMARY OF THE INVENTION

It is an object of the present invention to provide methods for detecting the presence of *Mycobacterium tuberculosis* Complex ("MT complex") nucleic acids in a test sample. Within certain aspects, the present invention provides a method wherein MT nucleic acids from a test sample are amplified using oligonucleotide primers to generate an amplicon and amplification of the amplicon is detected.

In one aspect, the present invention provides a method for determining if a sample contains *Mycobacterium tuberculosis* complex (MT complex) nucleic acids. The method involves:

(a) contacting the sample with forward and reverse oligonucleotide primers, under conditions suitable for amplification of all or a portion thereof of the IS6110 preferential locus (ipl) 3'-flanking region, if present in the sample; to generate MT amplicons, and (b) detecting the amplification, wherein detecting indicates the presence of *Mycobacterium tuberculosis* complex (MT complex) nucleic acids in the sample.

An exemplary sequence of an ipl 3'-flanking region is set forth in SEQ ID NO:5. In preferred embodiments, the ipl 3'-flanking region is 90% identical to SEQ ID NO:5. In more preferred embodiments, ipl 3'-flanking region is 95% identical to SEQ ID NO:5. In more preferred embodiments, ipl 3'-flanking region is 99% identical to SEQ ID NO:5. In most preferred embodiments, ipl 3'-flanking region is 100% identical to SEQ ID NO:5.

In another aspect, the present invention provides a method involving:

(a) contacting the sample with forward and reverse oligonucleotide primers, the forward oligonucleotide primer including the sequence of SEQ ID NO:1, the reverse oligonucleotide primer including the sequence of SEQ ID NO:2, under conditions suitable for amplification of a region of MT complex nucleic acid flanked by the forward and reverse oligonucleotide primers, if present in the sample; to generate MT complex amplicons; and (b) detecting the amplification of the MT complex amplicons, wherein detecting said region indicates the presence of *Mycobacterium tuberculosis* complex nucleic acids in the sample.

In a further aspect, the present invention provides a method for determining if a sample contains *Mycobacterium tuberculosis* complex (MT complex) nucleic acids. The method involves:

(a) contacting the sample with a forward oligonucleotide primer including a sequence of 15 or more nucleotides from within a 50 base segment of the ipl 3'-flanking region that includes the sequence set forth in SEQ ID NO:1 and a reverse oligonucleotide primer including a sequence of 15 or more nucleotides from within a 50 base segment of the ipl 3'-flanking region that includes the sequence set forth in SEQ ID NO:2 under conditions suitable for amplification of all or a portion of the ipl 3'-flanking region if present in the sample to generate MT complex amplicons; and (b) detecting said amplicons, wherein detecting indicates the presence of *Mycobacterium tuberculosis* complex (MT complex) nucleic acids in the sample.

In other aspects the invention provides methods to detect the amplicon in which it hybridizes to a specific oligonucleotide probe which may be labeled. In one embodiment, the probe may be labeled with a fluorescent reporter dye and a quencher dye. Upon hybridization to the amplicon, the oligonucleotide probe is cleaved by the nuclease activity of the polymerase and an increase in fluorescence is detected.

In other related aspects the invention provides methods of detecting the amplicon involving:
(a) hybridizing said MT complex amplicons with an oligonucleotide probe comprising the sequence set forth in SEQ ID NO:3 in the presence of an enzyme that cleaves the probe when the probe hybridizes to said MT complex nucleic acids, wherein the probe is conjugated to a detectable label that generates a detectable signal upon cleavage; and
(b) detecting a signal from the detectable label, wherein the signal from the detectable label indicates the presence of MT complex nucleic acids in the test sample.

As used herein, the term "detecting" used in context of detecting a signal from a detectable label to indicate the presence of MT complex nucleic acids in the sample does not require the method to provide 100% sensitivity and 100% specificity. As is well known, "sensitivity" is the probability that a test is positive, given that the person has the disease, while "specificity" is the probability that a test is negative, given that the person does not have the disease. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

Amplification primers may be designed for amplifying regions of the MT complex genome. In one approach, a primer pair is designed to specifically hybridize to the 156110 preferential locus (ipl) 3'-flanking sequence of the *M. tuberculosis* genome. An exemplary sequence of ipl including the 3'-flanking sequence, GenBank Accession No. X95799, is presented herein as SEQ ID NO:4, however analogous sequences containing the ipl locus and flanking regions (e.g., GenBank Accession Nos. X98149, X98151, X98153, X98156, or X98158) can be used as well. An exemplary sequence of an ipl 3'-flanking sequence is presented in SEQ ID NO:5. For example, a forward primer is designed to specifically hybridize to ipl 3'-flanking sequence (SEQ ID NO:5) between nucleotides 1 and 140, more preferably between positions 50 and 130, and most preferably between 90 and 130. A reverse primer is designed to specifically hybridize to 3'-flanking sequence (SEQ ID NO:5) between positions 165 and 383, more preferably between 165 and 255, and most preferably between 165 and 205. One example is to use a primer pair to amplify a region of ipl 3'-flanking sequence from nucleotide 81 to 182; more specifically using a forward primer, SEQ ID NO:1 and a reverse primer, SEQ ID NO:2 to amplify a 102 bp region of MT complex nucleic acid.

Preferred oligonucleotides which may be used as MT complex amplification primers include SEQ ID NO:1 (CTCGGTGAGAAGACCGTCA) and SEQ ID NO:2 (GTCCTCGATGCCCCAGAT). Other preferred oligonucleotide primers are approximately 15-100 nucleotides in length and comprise SEQ ID NO:1 or SEQ ID NO:2. Still other preferred oligonucleotide primers include an oligonucleotide sequence that hybridizes to the complement of a 15-100 nucleotide sequence including SEQ ID NO:1 or SEQ ID NO:2. Such oligonucleotides may be substantially purified.

| Sequence Name | SEQ ID NO: | Sequence |
|---|---|---|
| Forward Oligonucleotide Primer | SEQ ID NO: 1 | CTCGGTGAGAAGACCGTCA |
| Reverse Oligonucleotide Primer | SEQ ID NO: 2 | GTCCTCGATGCCCCAGAT |
| Oligonucleotide Probe | SEQ ID NO: 3 | AGCTCGAGGCCGAACTGTTCAC |

SEQ ID NO:1 can be used as a forward PCR amplification primer for amplifying a region of MT nucleic acid. SEQ ID NO:2 can be used as a reverse PCR amplification primer for amplifying a region of MT complex nucleic acid.

SEQ ID NO:3 can be used as an oligonucleotide probe. The probe may be labeled. Other oligonucleotide probes can be designed which are between about 10 and about 100 nucleotides in length and hybridize to the amplified region. Oligonucleotides probes are preferably 15 to 70 nucleotides; more preferably 15-60 nucleotides in length; and most preferably 15-25 nucleotides in length.

As used herein, the term "ipl 3'-flanking region" refers to nucleotides 268 through 650 of GenBank Accession No. X95799 (SEQ ID NO:4) and is exemplified in SEQ ID NO:5. The ipl locus is a stretch of 267 nucleotides, corresponding to nucleotides 1-267 of SEQ ID NO:4, which has been shown to contain 6 sites for IS6110 insertion. No insertion sites have been found in the ipl 3'-flanking region.

As used herein, the term "MT complex nucleic acids" refers to DNA and/or RNA containing a contiguous sequence from a *Mycobacterium tuberculosis* complex genome, or the complement thereof. The MT complex of organisms includes organisms which are closely related species of the genus *Mycobacterium* and which cause a tuberculosis-like syndrome. MT complex organisms share a high degree of evolutionary conservation as exemplified by their high degree of interstrain DNA homology, conservation of 16S rRNA gene sequence and 16S to 23S ribosomal RNA (rDNA) intergenic spacer sequences, limited diversity as measured by multilocus enzyme electrophoresis (MLEE), similarity of genomic restriction fragment analysis, and virtual lack of antigenic variation. MT complex organisms include but are not limited to *Mycobacterium* species *M. tuberculosis, M. bovis, M. bovis* BCG, *M. Africanum, M. Microti*, and *M. canettii*. MT complex nucleic acids may be MT complex genomic DNA, MT complex messenger RNA, or the complement of these sources, obtained by any method including obtaining the nucleic acid from a biological source, synthesizing the nucleic acid in vitro, or amplifying the nucleic acid by any method known in the art. Individual *Mycobacterium* species of the MT complex of organisms may be identified by DNA analysis as is well known in the art. See Khye et al., J Clin Microbiol. 2001 October; 39(10):3705-8. ("PCR-Restriction Analysis of the hsp65 Gene").

As used herein, the term "sample" or "test sample" refers to any liquid or solid material believed to contain MT nucleic acids. In preferred embodiments, a test sample is obtained from a biological source (i.e., a "biological sample"), such as cells in culture or a tissue sample from an animal, most preferably, a human. Preferred sample tissues include, but are not limited to, sputum, bronchial wash, blood, bone marrow, body fluids, cerebrospinal fluid, urine, gastric aspirate, plasma, serum, or tissue (e.g. biopsy material). The term "patient sample" as used herein refers to a tissue sample obtained from a human seeking diagnosis or treatment of a disease related to a *M. tuberculosis* infection.

As used herein, the term "oligonucleotide" refers to a short polymer composed of deoxyribonucleotides, ribonucleotides or any combination thereof. Oligonucleotides of the invention are generally between about 10 and about 100 nucleotides in length. Oligonucleotides are preferably 15 to 70 nucleotides long, with 20 to 26 nucleotides being the most common. The single letter code for nucleotides is as described in the U.S. Patent Office Manual of Patent Examining Procedure, section 2422, table 1. In this regard, the nucleotide designation "R" means guanine or adenine, "Y" means thymine (uracil if RNA) or cytosine; and "M" means adenine or cytosine. An oligonucleotide may be used as a primer or as a probe.

As used herein, the term "substantially purified" in reference to oligonucleotides does not require absolute purity. Instead, it represents an indication that the sequence is relatively more pure than in the natural environment. Such oligonucleotides may be obtained by a number of methods including, for example, laboratory synthesis, restriction enzyme digestion or PCR. A "substantially purified" oligonucleotide is preferably greater than 50% pure, more preferably at least 75% pure, and most preferably at least 95% pure.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

As used herein, the term "hybridize" or "specifically hybridize" refers to a process where two complementary nucleic acid strands anneal to each other under appropriately stringent conditions. Hybridizations are typically and preferably conducted with probe-length nucleic acid molecules, preferably 20-100 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

The term "flanking" as used herein means that a primer hybridizes to a target nucleic acid adjoining a region of interest sought to be amplified on the target. The skilled artisan will understand that preferred primers are pairs of primers that hybridize 3' from a region of interest, one on each strand of a target double stranded DNA molecule, such that nucleotides may be add to the 3' end of the primer by a suitable DNA polymerase.

The term "complement" as used herein means the complementary sequence to a nucleic acid according to standard Watson/Crick pairing rules. A complement sequence can also be a sequence of RNA complementary to the DNA sequence or its complement sequence, and can also be a cDNA.

The term "coding sequence" as used herein means a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

The term "non-coding sequence" as used herein means a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

The term "amplification" or "amplify" as used herein means one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4):852-6, 858, 860 passim.

As used herein, a "primer" for amplification is an oligonucleotide that specifically anneals to a target nucleotide sequence. The 3' nucleotide of the primer should be identical to the target sequence at a corresponding nucleotide position for optimal amplification.

"Sense strand" means the strand of double-stranded DNA (dsDNA) that includes at least a portion of a coding sequence of a functional protein. "Anti-sense strand" means the strand of dsDNA that is the reverse complement of the sense strand.

As used herein, a "forward primer" is a primer that anneals to the anti-sense strand of dsDNA. A "reverse primer" anneals to the sense-strand of dsDNA.

As used herein, sequences that have "high sequence identity" have identical nucleotides at least at about 50% of aligned nucleotide positions, preferably at least at about 58% of aligned nucleotide positions, and more preferably at least at about 76% of aligned nucleotide positions.

As used herein, "about" means plus or minus 10%.

BRIEF DESCRIPTION OF THE FIGURES

FIG. 1. Nucleotide sequence of Genbank Accession No. X95799 (SEQ ID NO:4). The sequence of ipl is underlined; the ipl 3'-flanking region is shaded (SEQ ID NO:5).

FIG. 2. Multiple sequence alignment of sequences containing the ipl locus and flanking regions (GenBank Accession Nos. X95799, X98149, X98151, X98153, X98156, and X98158). The ipl 3'-flanking regions are shaded.

DETAILED DESCRIPTION OF THE INVENTION

In accordance with the present invention, there are provided methods for detecting the presence of *M. tuberculosis* nucleic acids in a sample.

Sample Preparation

The method may be performed using any biological sample. Biological samples may be obtained by standard procedures and may be used immediately or stored (e.g., the sample may be frozen at about −20° C. to about −80° C.) for later use. The presence MT complex nucleic acids in a sample can be determined by amplifying target regions within MT complex nucleic acids. Thus, any liquid or solid material believed to contain MT complex nucleic acids can be an appropriate sample. Preferred sample tissues include blood, bone marrow, body fluids, cerebrospinal fluid, urine, gastric aspirate and others.

Biological samples may be obtained from patients suspected of having an *M. tuberculosis* infection, or having any of a wide spectrum of diseases related to *M. tuberculosis* infection, for example, a subclinical carrier state. Although the pathogenetic role of *M. tuberculosis* is not clear, it is also associated with such diseases as sarcoidosis and Crohn's disease, as well as different auto-immune diseases, such as auto-immune dermatitis, rheumatoid arthritis and diabetes.

Nucleic acids from *M. tuberculosis* may be extracted from tissue samples prior to amplification. Samples are pre-treated to lyse the mycobacteria, releasing the nucleic acids. Viscous samples such as sputum are generally liquefied by adding a solution of N-acetyl-1-cysteine (NALC) that is resuspended in a solution of citrate and NaOH. Addition of this solution to the sputum breaks it up and liquefies it. Alternatively, viscous samples are treated with DTT, incubated at 65° C. for 30 minutes, centrifuged, and the supernatant removed. Once the sample is liquefied, bacteria are pelleted, resuspended in a neutralizing buffer, and then can be subjected to lysis and nucleic acid extraction.

In an alternate pre-treatment protocol, lysis buffer (MagNA Pure System, Roche) is added in an equal volume of lysis buffer to the sputum. The sample is mixed by vortex and incubated for 15 min at 95° C. At this point, the sputum is sufficiently broken down (the viscosity is decreased enough to pipette), and it can be transferred to an automated DNA extraction instrument (e.g., MagNA Pure). Lysis of the mycobacteria can also be achieved by various methods known in the art (e.g., treatment with proteinase K and lysis buffer, freeze-thaw cycling, or sonication) (Buck et al. J. Clin. Microbiol. 30:1331-1334, 1992). Various commercial nucleic acid purification kits, such as MagNA Pure LC DNA Isolation Kit III or Total Nucleic Acid Isolation Kit (Roche) and related methods known to the skilled artisan and may be used to isolate MT complex nucleic acids from the pre-treated samples.

Amplification of *M. tuberculosis* Nucleic Acids of Interest

Target samples or isolated nucleic acids may be amplified by various methods known to the skilled artisan. Preferably, PCR is used to amplify *M. tuberculosis* nucleic acids of interest. In this method, two or more oligonucleotide primers that flank and anneal to opposite strands of a nucleic acid of interest are repetitively annealed to their complementary sequences, extended by a DNA polymerase (e.g., AmpliTaq Gold polymerase), and heat denatured, resulting in exponential amplification of the target nucleic acid sequences. Cycling parameters can be varied, depending on the length of nucleic acids to be extended. The skilled artisan is capable of designing and preparing primers that are appropriate for amplifying a target sequence. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well known to the person of ordinary skill. For example, the length of a short nucleic acid or oligonucleotide can relate to its hybridization specificity or selectivity.

Assay controls may be used in the assay for detecting *mycobacterium tuberculosis* complex nucleic acid. Positive controls with high concentrations (e.g. 100,000 organisms/ml) and low concentrations (1,000 organisms/ml) of an avirulent *M. tuberculosis* stain may be used (e.g. ATCC #25177). An internal positive amplification control (IPC) can be included in the sample and may be introduced as part of a primer/probe mastermix.

Detection of Amplified *M. tuberculosis* Nucleic Acids

A probe oligonucleotide, complementary to the amplified region of MT complex nucleic acid, is used to detect the amplification of *M. tuberculosis* nucleic acids. The probe may be detectably labeled by methods known in the art. The binding of a probe to the amplified region of the MT complex nucleic acid may be determined by hybridization as is well known in the art. Hybridization may be detected in real time or in non-real time.

One general method for real time PCR uses fluorescent probes such as the TaqMan® probes, molecular beacons and scorpions. Real-time reverse-transcriptase (RT) PCR quantitates the initial amount of the template with more specificity, sensitivity and reproducibility, than other forms of quantitative reverse transcriptase PCR, which detect the amount of final amplified product. Real-time RT-PCR does not detect the size of the amplicon. The probes employed in TaqMan® and molecular beacon technologies are based on the principle of fluorescence quenching and involve a donor fluorophore and a quenching moiety.

The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e. collisional) quenching or by Förster or fluorescence resonance energy transfer ("FRET"). Quenching by FRET is generally used in TaqMan® probes while proximal quenching is used in molecular beacon and scorpion type probes.

In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a higher wavelength. Proximal quenching requires very close positioning of the donor and quencher moiety, while FRET quenching, also distance related, occurs over a greater distance (generally 1-10 nm, the energy transfer depending on $R^{-6}$, where R is the distance between the donor and the acceptor). Thus, when FRET quenching is involved, the quenching moiety is an acceptor fluorophore that has an excitation frequency spectrum that overlaps with the donor emission frequency spectrum. When quenching by FRET is employed, the assay may detect an increase in donor fluorophore fluorescence resulting from increased distance between the donor and the quencher (acceptor fluorophore) or a decrease in acceptor fluorophore emission resulting from increased distance between the donor and the quencher (acceptor fluorophore).

TaqMan® probes (Heid et al., 1996) use the fluorogenic 5' exonuclease activity of Taq polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo)benzoic acid (DABCYL). See Tyagi et al., Nature Biotechnology 16:49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase (e.g. reverse transcriptase) replicates a template on which a TaqMan® probe is bound, its 5' exonuclease activity cleaves the probe. This ends the activity of quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

TaqMan® assay uses universal thermal cycling parameters and PCR reaction conditions. Because the cleavage occurs only if the probe hybridizes to the target, the fluorescence detected originates from specific amplification. The process of hybridization and cleavage does not interfere with the exponential accumulation of the product. One specific requirement for fluorogenic probes is that there be no G at the 5' end. A 'G' adjacent to the reporter dye quenches reporter fluorescence even after cleavage.

Other methods of probe hybridization detected in real time can be used for detecting amplification of MT complex nucleic acids. For example, the commercially available MGB Eclipse™ probes (Epoch Biosciences), which do not rely on a probe degradation can be used. MGB Eclipse™ probes work by a hybridization-triggered fluorescence mechanism. MGB Eclipse™ probes have the Eclipse™ Dark Quencher and the MGB positioned at the 5'-end of the probe. The fluorophore is located on the 3'-end of the probe. When the probe is in solution and not hybridized, the three dimensional conformation brings the quencher into close proximity of the fluorophore, and the fluorescence is quenched. However, when the probe anneals to a target sequence, the probe is unfolded, the quencher is moved from the fluorophore, and the resultant fluorescence can be detected.

Suitable donor fluorophores include 6-carboxyfluorescein (FAM), tetrachloro-6-carboxyfluorescein (TET), 2'-chloro-7'-phenyl-1,4-dichloro-6-carboxyfluorescein (VIC), and the like. Suitable quenchers include tetra-methylcarboxyrhodamine (TAMRA) 4-(4-dimethylaminophenylazo)benzoic acid ("DABCYL" or a DABCYL analog) and the like. Tetramethylrhodamine (TMR) or 5-carboxyrhodamine 6G (RHD) may be combined as donor fluorophores with DABCYL as quencher. Multiplex TaqMan assays can be performed using multiple detectable labels each comprising a different donor and quencher combination. Probes for detecting amplified sequence in real time may be stored frozen (−10° to −30° C.) as 100 µM stocks. TaqMan probes are available from Applied BioSystems (4316032).

In a preferred embodiment, real time PCR is performed using TaqMan® probes in combination with a suitable amplification/analyzer such as the ABI Prism 7900HT Sequence Detection System. The ABI PRISM® 7900HT Sequence Detection System is a high-throughput real-time PCR system that detects and quantitates nucleic acid sequences. Briefly, TaqMan™ probes specific for each allele are included in the PCR assay. These probes contain a reporter dye at the 5' end and a quencher dye at the 3' end. Each allele specific probe is conjugated with a different fluorescent reporter dye. During PCR, the fluorescently labeled probes bind specifically to their respective target sequences; the 5' nuclease activity of Taq polymerase cleaves the reporter dye from the probe and a fluorescent signal is generated. The increase in fluorescence signal is detected only if the target sequence is complementary to the probe and is amplified during PCR. A mismatch between probe and target greatly reduces the efficiency of probe hybridization and cleavage. The ABI Prism 7700HT or 7900HT Sequence detection System measures the increase in fluorescence during PCR thermal cycling, providing "real time" detection of PCR product accumulation.

Real Time detection on the ABI Prism 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually.

The examples below illustrate a standard protocol for performing PCR and analyzing in real time. The TaqMan system of primer labeling is a preferred method of real time detection of PCR amplicons. The following examples serve to illustrate the present invention. These examples are in no way intended to limit the scope of the invention.

Example 1

Primer/Probe Mastermix Preparation

A stock solution of primer and probe mastermix was prepared by mixing each of the stock solutions as shown in Table 1.

TABLE 1

Primer/Probe Mastermix.

|  | ul/reaction | volume/1000 reactions | final concentration per reaction |
|---|---|---|---|
| Sterile Nuclease Free Water | 7.95 | 7.95 ml |  |
| 10x Exo IPC* Mix (ABI #4308323) | 5.0 | 5.0 ml | 1 x |
| 50x Exo IPC DNA (ABI#4308323) | 1.0 | 1.0 ml | 1 x |
| Forward Primer (100 µM) | 0.25 | 0.25 ml | 500 nM |
| Reverse Primer (100 µM) | 0.25 | 0.25 ml | 500 nM |
| Oligonucleotide Probe (100 µM) | 0.05 | 50 µl | 100 nM |
| Total | 14.5 µl | 14.5 ml |  |

*Exo IPC: Exogenous internal positive control

The mastermix stock solution was dispensed into 580 µl aliquots. Each aliquot is sufficient for 38 reactions. This solution can be stored at −20° C. for 1 year from the date of preparation.

Example 2

Preparation and DNA Extraction of Clinical Samples

Biological samples (e.g., sputum, bronchial wash, blood, bone marrow, body fluids, tissue, CSF, urine, or gastric aspirate) of a volume of 0.3-0.8 ml were collected. Gastric aspirate samples were neutralized with sodium carbonate within four hours of collection. Viscous samples (e.g., sputum and bronchial wash) were liquefied by adding a solution of N-acetyl-1-cysteine (NALC) that is resuspended in a solution of citrate and NaOH. Addition of this solution to the sample liquefied it. Once the sample was liquefied, bacteria were pelleted, resuspended in a neutralizing buffer, and subjected to the lysis procedure. All other samples were added directly to the lysis buffer.

130 µl of lysis buffer and 20 µl of proteinase K were added to 100 µl of the biological sample and mixed thoroughly by vortexing for approximately 10 s. Reagents were from the MagNA Pure LC DNA Isolation Kit III (Bacteria, Fungi) (Roche Cat. #3 264 785). The samples were incubated at 65° C. for 10 minutes, then at 95° C. for 10 minutes. The samples were cooled for 5 minutes at room temperature.

DNA was extracted from controls and treated biological samples using the MagNA Pure LC automated nucleic acid extraction system and the protocol for the MagNA Pure LC DNA Isolation Kit III (Bacteria, Fungi). 200 µl of control (Hi Pos, Low Pos, or negative) or biological sample was loaded into the sample cartridge.

Example 3

DNA Amplification

To prepare the final mastermix, 1 ml of ABI 2× Mastermix (ABI #4304437), and 20 µl AmpliTaq Gold was added to a single vial (580 µl) of stock primer/probe mastermix. The resulting solution was mixed by pulse vortex 10 times. 40 µl was dispensed into each well of a 96-well plate to be used for PCR. The extracts from the control or biological samples were added to individual wells (10 µl/well) containing the final mastermix. The plate was sealed and transferred to the ABI 7700 (or 7900HT) sequence detector.

The thermocycler conditions were as follows:
Stage 1: Hold at 50.0° C. for 2 min.
Stage 2: Hold at 95° C. for 10 min.
Stage 3: Cycle from 95.0° C. for 15 s to 60° C. for 1 min, 43 cycles.
Sample volume: 50 µl.

Example 4

Data Analysis

The assay as described has been used to detect *M. tuberculosis* complex nucleic acids in a variety of clinical specimens, including sputum, bronchial lavage, blood, and urine. The assay results were reproducible over the course of multiple runs. Method comparison studies performed to detect *M. tuberculosis* from samples submitted from patients showing symptoms of tuberculosis were performed. This included a comparison with culture methodologies and with conventional (not real-time) PCR amplification assays. The results support the conclusion that the real-time PCR format described herein is both sensitive and specific, detecting specimens that were shown to be positive for *M. tuberculosis* by culture. In addition, the assay in a real-time PCR format was shown to be more sensitive than the non-real-time PCR format.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

That which is claimed is:

1. A kit for identifying *Mycobacterium tuberculosis* complex (MT complex) nucleic acid in a sample, said kit comprising:
   (a) a forward oligonucleotide primer that hybridizes to a sequence of at least 15 nucleotides of nucleotide 81-99 of SEQ ID NO: 5 or the complement of a sequence of at least 15 nucleotides of nucleotides 81-99 of SEQ ID NO: 5, and
   (b) a reverse oligonucleotide primer that hybridizes to a sequence of at least 15 nucleotides 165-182 of SEQ ID NO: 5 or the complement of a sequence of at least 15 nucleotides of nucleotides 165-182,
   and further comprising an oligonucleotide probe comprising SEQ ID NO: 3 or the complement of SEQ ID NO: 3, wherein said oligonucleotide probe is labeled with a donor fluorophore and a quenching moiety.

2. A kit according to claim 1 wherein said forward oligonucleotide primer comprises SEQ ID NO: 1 and said reverse oligonucleotide primer comprises SEQ ID NO: 2.

3. A kit according to claim 1 wherein, said forward oligonucleotide primer comprises the sequence of SEQ ID NO: 1 and said reverse oligonucleotide primer comprises the sequence of SEQ ID NO: 2.

4. A kit according to claim 1 wherein said donor fluorophore is 6-carboxyfluorescein (6-FAM) and said quenching moiety is 6-carboxytetramethylrhodamine.

5. A kit for identifying *Mycobacterium tuberculosis* complex (MT complex) nucleic acid in a sample, said kit comprising a forward oligonucleotide primer consisting of SEQ ID NO: 1 labeled with a fluorophore.

6. A kit for identifying *Mycobacterium tuberculosis* complex (MT complex) nucleic acid, said kit comprising a reverse oligonucleotide primer consisting of SEQ ID NO: 2 labeled with a fluorophore.

7. An isolated oligonucleotide primer or probe consisting of a sequence labeled with a donor fluorophore or a quenching moiety wherein the sequence is selected from the group consisting of SEQ ID NO: 1-3 or the complement of each of SEQ ID NO: 1-3.

8. The isolated oligonucleotide primer of claim 7 wherein the sequence consists of SEQ ID NO: 1.

9. The isolated oligonucleotide primer of claim 7 wherein the sequence consists of SEQ ID NO: 2.

10. The isolated oligonucleotide probe of claim 7 wherein the sequence consists of SEQ ID NO: 3.

* * * * *